United States Patent [19]

Yoshitake et al.

[11] Patent Number: 4,898,959

[45] Date of Patent: Feb. 6, 1990

[54] METHOD FOR THE PREPARATION OF BETA-SUBSTITUTED ALLYLSILANE

[75] Inventors: Makoto Yoshitake; Shinichiro Yamane; Akihiko Shirahata, all of Chiba, Japan

[73] Assignee: Toray Silicone Company, Ltd., Tokyo, Japan

[21] Appl. No.: 287,411

[22] Filed: Dec. 20, 1988

[30] Foreign Application Priority Data

Dec. 24, 1987 [JP] Japan .................................. 62-327628

[51] Int. Cl.$^4$ ................................................. C07F 7/08
[52] U.S. Cl. .................................................... 556/466
[58] Field of Search ......................................... 556/466

[56] References Cited

U.S. PATENT DOCUMENTS 3,223,686  12/1965  Matta et al. ...................... 556/466 X

FOREIGN PATENT DOCUMENTS 148791  8/1984  Japan .................................. 556/466

Primary Examiner—Paul F. Shaver
Attorney, Agent, or Firm—George A. Grindahl

[57] ABSTRACT

Beta-substituted allylsilanes are synthesized in a one-step process from readily available starting materials by the reaction of a specific carboxylic acid ester or acid anhydride with a specific alkoxy group-containing Grignard reagent in an organic solvent. The resulting allylsilanes are useful as allyl transfer reagents for electrophilic reagents such as ketones, carboxylic acid chlorides, etc.

5 Claims, No Drawings

METHOD FOR THE PREPARATION OF BETA-SUBSTITUTED ALLYLSILANE

BACKGROUND OF THE INVENTION

The present invention relates to a method for the preparation of allylsilanes, which are useful as allyl transfer reagents for electrophilic reagents such as ketones, carboxylic acid chlorides, etc. More specifically, the present invention relates to a method for the preparation of beta-substituted allylsilanes.

Allylsilanes are often used with electrophilic reagents such as ketones, carboxylic acid chlorides, etc. (refer to A. Hosomi and H. Sakurai, Tetrahedron Letters).

Furthermore, in addition to the unsubstituted allylsilanes, this reaction has also been investigated and widely applied for allylsilanes variously substituted at the allyl group's alpha, beta, and gamma positions (refer to Ernest W. Colvin, Silicon in Organic Synthesis, pp. 104 to 117, Butterworths).

However, substituted allylsilanes have generally been difficult to prepare, and the preparative methods themselves vary according to the type and position of the substituent group. Among these, preparative methods for beta-substituted allylsilanes have proven to be particularly complex, and have involved lengthy campaigns comprising at least two steps. Furthermore, it has been necessary to use special starting materials.

The present inventors achieved the present invention as the result of extensive research directed at solving the problems arising with methods for the preparation of beta-substituted allylsilanes.

BRIEF SUMMARY OF THE INVENTION

It is an object of the present invention to provide a novel method for the preparation of beta-substituted allylsilanes.

Specifically, the present invention comprises a method for the preparation of beta-substituted allylsilane with the general formula (IV)

$$R^1CCH_2SiR^3R^4R^5 \quad (IV)$$
$$\parallel$$
$$CH_2$$

said method comprising reacting, in an organic solvent, a Grignard reagent with the general formula (III)

$$R^3R^4R^5SiCH_2MgX \quad (III)$$

with a substrate compound selected from the group consisting of an acid anhydride with the general formula (II)

$$(R^1CO)_2O \quad (II)$$

and a carboxylic acid ester with the general formula (I)

$$R^1COOR^2 \quad (I)$$

where, in the preceding formulae (I), (II), (III), and (IV), $R^1$ is a hydrogen atom or a hydrocarbon group having 1 to 20 carbon atoms, $R^2$ is a hydrocarbon group having 1 to 4 carbon atoms, $R^3$, $R^4$, and $R^5$ are independently selected from the group consisting of hydrocarbon groups having 1 to 3 carbon atoms or alkoxy groups, at least one of $R^3$, $R^4$, and $R^5$ being an alkoxy group having at least 3 carbon atoms, and X is a halogen atoms.

DETAILED DESCRIPTION OF THE INVENTION

To explain the preceding in greater detail, $R^1$ in the carboxylic acid ester to be used in the present invention with the above general formula (I) comprises the hydrogen atom or a hydrocarbon group having 1 to 20 carbon atoms, such as the methyl group, ethyl group, propyl group, alpha-methylvinyl group, phenyl group, beta-phenylvinyl group, and benzyl group. $R^2$ is a hydrocarbon group having 1 to 4 carbon atoms such as the methyl group, ethyl group, propyl group, and butyl group.

Concrete examples of this carboxylic acid ester are ethyl formate, propyl formate, butyl formate, methyl acetate, ethyl acetate, methyl propionate, ethyl propionate, methyl methacrylate, methyl butyrate, ethyl butyrate, methyl benzoate, ethyl benzoate, methyl cinnamate, methyl phenylacetate, and ethyl phenylacetate.

With regard to the acid anhydride to be used in the present invention, $R^1$ in the above general formula (II) again is the hydrogen atom or a hydrocarbon group having 1 to 20 carbon atoms as above.

Concrete examples of this acid anhydride are acetic anhydride, propionic anhydride, butyric anhydride, and benzoic anhydride.

Considering the alkoxy group-containing Grignard reagent used in the present invention, $R^3$, $R^4$, and $R^5$ in the above general formula (III) comprise hydrocarbon groups having 1 to 3 carbon atoms, e.g. methyl, ethyl and propyl, or an alkoxy group wherein at least one of these is an alkoxy group having at least 3 carbon atoms such as, for example, n-propoxy (n-PrO), isopropoxy (i-PrO), n-butoxy (n-BuO), sec-butoxy, (s-BuO), isobutoxy (i-BuO) and n-pentoxy (PentO).

Compounds with the following chemical structures are concrete examples of this alkoxy group-containing Grignard reagent.

| Me<br>n-PrOSiCH$_2$MgCl<br>Me | Me<br>n-PrOSiCH$_2$MgBr<br>Me | Me<br>n-PrOSiCH$_2$MgI<br>Me |
|---|---|---|
| Et<br>n-PrOSiCH$_2$MgCl<br>Et | Pr<br>n-PrOSiCH$_2$MgCl<br>Pr | Me<br>i-PrOSiCH$_2$MgCl<br>Me |
| Me<br>i-PrOSiCH$_2$MgBr<br>Me | Me<br>i-PrOSiCH$_2$MgI<br>Me | Et<br>i-PrOSiCH$_2$MgCl<br>Et |
| Pr<br>i-PrOSiCH$_2$MgCl<br>Pr | Me<br>n-BuOSiCH$_2$MgCl<br>Me | Me<br>i-BuOSiCH$_2$MgCl<br>Me |
| Me<br>s-BuOSiCH$_2$MgCl<br>Me | Me<br>PentOSiCH$_2$MgCl<br>Me | (n-PrO)$_2$SiCH$_2$MgCl<br>Me |
| (n-PrO)$_2$SiCH$_2$MgCl<br>Et | (n-PrO)$_2$SiCH$_2$MgCl<br>Pr | (i-PrO)$_2$SiCH$_2$MgCl<br>Me |
| (i-PrO)$_2$SiCH$_2$MgCl<br>Et | (i-PrO)$_2$SiCH$_2$MgCl<br>Pr | (n-BuO)$_2$SiCH$_2$MgCl<br>Me |
| (i-BuO)$_2$SiCH$_2$MgCl<br>Me | (s-BuO)$_2$SiCH$_2$MgCl<br>Me | |

While the quantity of use of this reagent is not specifically restricted, in general it will be advantageous to conduct the reaction within the range of 2 to 3 moles per 1 mole of the above carboxylic acid ester or acid anhydride.

The Grignard reagent that is used in the method of this invention is prepared in the usual manner common to the preparation of Grignard reagents in general, as shown in the Examples disclosed below.

The organic solvent to be used in the present invention may be any organic solvent which dissolves the alkoxy groupcontaining Grignard reagent and the aforementioned carboxylic acid ester or acid anhydride, and no particular restriction applies in this regard. However, in general ether-type organic solvents will be used, for example, diethyl ether, dipropyl ether, dibutyl ether, tetrahydrofuran, dioxane, etc. The quantity of use of the solvent falls with the range of 1 to 100-fold of the total volume of the alkoxy group-containing Grignard reagent plus carboxylic acid ester or acid anhydride.

Within the present invention, the reaction is brought about by mixing the various components as described above, and the reaction temperature generally falls within the range of minus 80° C. to plus 100° C., and preferably falls within the range of 0° C. to plus 80° C.

While the reaction time will vary with the type and quantity of use of the carboxylic acid ester, acid anhydride, alkoxy group-containing Grignard reagent, and organic solvent, in general it will fall into the range of 0.5 hours to 50 hours.

In the present invention, the reaction mixture is extracted with water and separated upon completion of the reaction. The beta-substituted allylsilane reaction product is then purified, and in this regard one has recourse to purification techniques familiar to the art, for example, distillation, chromatography, etc.

The present invention will be explained in greater detail in the following reference to illustrative examples. In the examples, Me=methyl and Ph=phenyl.

EXAMPLE 1

10.21 g magnesium turnings was added to a 500 mL three-neck flask equipped with a reflux condenser, stirrer, and thermometer, and the reactor's atmosphere was then substituted with nitrogen. 5 mL of a solution of 68.37 g isopropoxydimethyl (chloromethyl) silane in 270 mL anhydrous tetrahydrofuran was dripped into the reactor, two drops ethylene bromide was then added, and a warming was confirmed. After confirming the occurrence of the Grignard reaction, the remaining 265 mL of the solution was dripped in over 1 hour with ice cooling. After completion of the addition, a solvent solution of the alkoxy group-containing Grignard reagent was obtained by stirring for 2 hours at room temperature. A solution of 27.23 g methyl benzoate dissolved in 50 mL anhydrous tetrahydrofuran was then dripped into this solvent solution over 1 hour. After completion of the addition, the reaction was brought to completion by stirring for 1 hour while heating under reflux. 50 mL saturated aqueous ammonium chloride was then slowly dripped into the reactor with ice cooling, and the reaction product was extracted by the addition of 50 mL tetrahydrofuran. After drying the extract solution over magnesium sulfate, it was distilled in vacuo to yield 39.4 g of a reaction product boiling at 98° to 99° C./3 mmHg. Measurement of the nuclear magnetic resonance spectrum confirmed this reaction product to be a compound with the chemical structure given below.

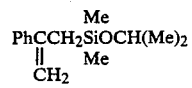

EXAMPLE 2

A reaction was conducted as in Example 1, but using 1 g methyl methacrylate in place of the 27.23 g methyl benzoate used in Example 1. The obtained reaction product was eluted by column chromatography (packed with Wakogel C-300, hexane elution) and analyzed as in Example 1. 0.86 g of the compound with the chemical structure given below was obtained.

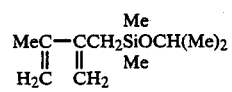

EXAMPLE 3

A reaction was run according to the procedure of Example 1, but using 1.66 g methyl cinnamate in place of the 27.23 g methyl benzoate used in Example 1. The obtained reaction product was eluted by column chromatography (packed with Wakogel C-300, hexane elution), and was analyzed as in Example 1. 1.89 g of the compound with the following chemical structure was obtained.

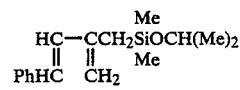

EXAMPLE 4

A reaction was run according to the procedure of Example 1, but using 1.02 g acetic anhydride in place of the 27.23 g methyl benzoate used in Example 1. The obtained reaction product was purified and analyzed as in Example 1, and 0.90 g of the compound with the chemical structure given below was obtained.

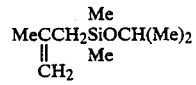

EFFECTS OF THE INVENTION

The present invention, as a consequence of the reaction of a specific carboxylic acid ester or acid anhydride with a specific alkoxy group-containing Grignard reagent in an organic solvent, is characterized by the high-yield preparation of beta-substituted allylsilanes, and is further characterized by the preparation of beta-substituted allylsilanes in one process from readily available starting materials.

That which is claimed is:

1. A method for the preparation of betasubstituted allylsilane with the general formula (IV)

said method comprising reacting, in an organic solvent, a Grignard reagent with the general formula (III)

$$R^3R^4R^5SiCH_2MgX \qquad (III)$$

with a substrate compound selected from the group consisting of an acid anhydride with the general formula (II)

$$(R^1CO)_2O \qquad (II)$$

and a carboxylic acid ester with the general formula (I)

$$R^1COOR^2 \qquad (I)$$

where, in the preceding formulae (I), (II), (III), and (IV), $R^1$ is a hydrogen atom or a hydrocarbon group having 1 to 20 carbon atoms, $R^2$ is a hydrocarbon group having 1 to 4 carbon atoms, $R^3$, $R^4$, and $R^5$ are independently selected from the group consisting of hydrocarbon groups having 1 to 3 carbon atoms or alkoxy groups, at least one of $R^3$, $R^4$, and $R^5$ being an alkoxy group having at least 3 carbon atoms, and X is a halogen atom.

2. A method according to claim 1 wherein the substrate compound comprises the acid anhydride.

3. A method according to claim 1 wherein the substrate compound comprises the carboxylic acid ester.

4. A method according to claim 1 wherein the Grignard reagent has the formula $(CH_3)_2CHOSi(CH_3)_2CH_2MgCl$.

5. A method according to claim 1 wherein the amount of Grignard reagent is equal to from 2 to 3 moles per 1 mole of the substrate compound.

* * * * *